(12) United States Patent
Uemura et al.

(10) Patent No.: US 6,730,911 B2
(45) Date of Patent: May 4, 2004

(54) METHOD AND APPARATUS FOR PAPER MATERIAL DISCRIMINATION WITH TWO NEAR-INFRARED LIGHTS

(75) Inventors: Toshiro Uemura, Nisshin (JP); Yoshitaka Takezawa, Hitachinaka (JP); Mitsunari Kano, Seto (JP); Junichi Katagiri, Naka (JP); Eiji Mizuno, Owariasahi (JP)

(73) Assignee: Hitachi, Ltd., Tokyo (JP)

(*) Notice: Subject to any disclaimer, the term of this patent is extended or adjusted under 35 U.S.C. 154(b) by 19 days.

(21) Appl. No.: 10/073,886

(22) Filed: Feb. 14, 2002

(65) Prior Publication Data

US 2002/0158201 A1 Oct. 31, 2002

(30) Foreign Application Priority Data

Feb. 15, 2001 (JP) ........................... 2001-037856

(51) Int. Cl.[7] .............................................. G01N 21/55
(52) U.S. Cl. ........................ 250/339.01; 250/339.1; 250/339.06
(58) Field of Search ................... 250/339.01, 339.1, 250/339.06, 339.12, 341.8, 340, 339.11

(56) References Cited

U.S. PATENT DOCUMENTS

| 3,851,175 A | | 11/1974 | Dahlin et al. |
| 4,800,279 A | * | 1/1989 | Hieftje et al. ......... 250/339.09 |
| 5,075,551 A | * | 12/1991 | Watanabe .............. 250/341.03 |
| 5,435,309 A | * | 7/1995 | Thomas et al. ............. 600/310 |
| 5,757,001 A | * | 5/1998 | Burns .................... 250/339.11 |
| 6,050,387 A | | 4/2000 | Iwaki |
| 6,272,440 B1 | * | 8/2001 | Shakespeare et al. ......... 702/85 |
| 6,281,498 B1 | * | 8/2001 | Fellows ................. 250/339.06 |
| 6,548,813 B1 | * | 4/2003 | Fijukawa et al. ......... 250/341.6 |

FOREIGN PATENT DOCUMENTS

| EP | 0-295486 | 12/1988 |
| EP | 0-453797 | 10/1991 |
| EP | 1-128178 | 8/2001 |
| JP | 06-333123 | 12/1994 |
| JP | 08-180189 | 7/1996 |
| JP | 09-231435 | 9/1997 |
| JP | 10-232166 | 9/1998 |
| JP | 11-139620 | 5/1999 |
| JP | 2000-339513 | 12/2000 |
| JP | 2000-259885 | 1/2001 |
| WO | 00/28303 | 5/2000 |

* cited by examiner

Primary Examiner—Constantine Hannaher
Assistant Examiner—Otilia Gabor
(74) Attorney, Agent, or Firm—Mattingly, Stanger & Malur, P.C.

(57) ABSTRACT

A bill discriminating method of discriminating a paper material independent of a light/dense pattern caused by a difference of manufacturing steps and discriminating a paper material of paper without being influenced by humidity or deterioration of the paper material is provided, Two kinds of infrared rays of different kinds of wavelengths are irradiated onto the paper, thereby discriminating the paper material of the paper by using an absorbance difference between photometric values.

23 Claims, 4 Drawing Sheets

METHOD AND APPARATUS FOR PAPER MATERIAL DISCRIMINATION WITH TWO NEAR-INFRARED LIGHTS

BACKGROUND OF THE INVENTION

The invention relates to a method and an apparatus for detecting paper material of paper and, more particularly, to a method and an apparatus for paper material discrimination of an apparatus which handles paper such as securities, bill, or the like.

As a method of detecting a paper material of paper, at disclosed in JP-A-8-180189, there is a technique made by paying attention to a peculiar structure of paper fibers which are formed in a manufacturing step of the paper. According to such a technique, a lattice-like light/dense pattern which is derived from the structure (regular pattern which is laced into paper) that is peculiar to a specific bill is fetched and data is analyzed, thereby discriminating the paper material. As disclosed in JP-A-11-139620, there is also a method of discriminating a paper material from a time that is required for conveying paper for a predetermined distance by using a principle such that friction upon conveyance differs depending on a paper material of a paper.

As disclosed in JP-A-10-232166, there is a technique regarding a discriminating method of a paper pack whereby a material of the paper containing no metal can be discriminated. According to such a technique, by irradiating a near-infrared light onto the paper pack and specifying a wavelength at a peak of absorbance of a wavelength of the non-infrared light that is peculiar to the material, a kind of paper pack is discriminated.

The lattice-like light/dense pattern to which the attention has been paid in JP-A-8-180189 is laced into the paper which is used for the bill to identify the authentic bill. However, even in case of the same paper material, if the manufacturing steps are different, the light/dense pattern changes. There is, consequently a problem such that the paper material cannot be precisely discriminated by one data analyzing method due to an influence by a variation of the lattice-like light/dense patterns. According to the technique of JP-A-11-139620, there is a problem such that since a degree of the friction or hardness of the paper fluctuates due to an influence by humidity, a deterioration of the paper material, or the like, such a technique can be applied only in a limited situation.

Further, according to the technique of JP-A10-232166, in order to specify the wavelength at the peak of the absorbance, amounts of all of the reflection lights within a range prom 800 nm to 2500 nm have to be obtained. There is, consequently, a problem such that a time which is required for such a purpose is too long with respect to the paper such as securities, bill, or the like in which a high speed process is necessary.

SUMMARY OF THE INVENTION

It is an object of the invention to provide a technique for discriminating a paper material independent of a light/dense pattern with is caused by a difference of manufacturing steps. Another object of the invention is to provide a technique for discriminating a paper material of paper without being influenced by humidity or paper material. Further another object of the invention is to provide a technique for making a precise discrimination of a paper material at a high speed. Other objects will be obviously understood from the following detailed description.

According to the invention, lights of different kinds of wavelengths are irradiated onto paper and absorbances of reflected lights are measured, thereby discriminating, the paper material of the paper from a difference between the absorbances. More specifically speaking, absorbances in two infrared lights of different wavelengths are obtained and the paper material is discriminated by a degree of difference between the absorbances, that is, an absorbance difference or an absorbance ratio.

Other objects, features and advantages of the invention will become apparent from the following description of the embodiment of the invention taken in conjunction with the accompanying drawings.

DETAILED DESCRIPTION OF EMODIMENTS

Figure 1:
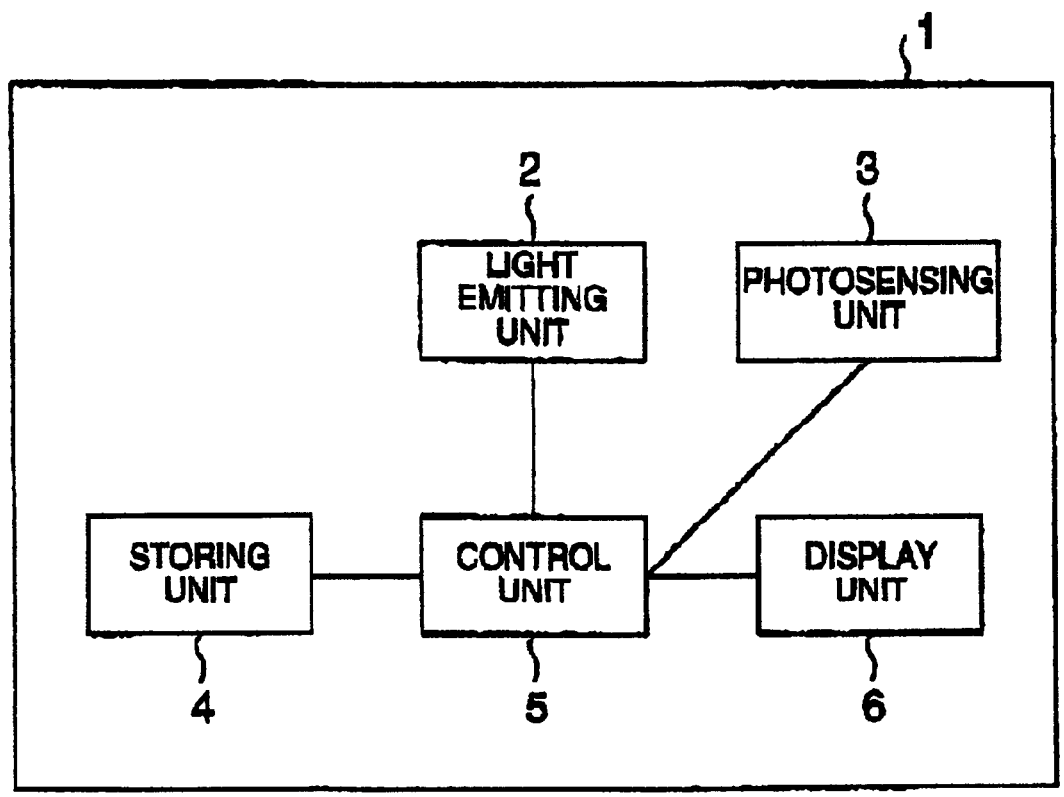
FIG. 1 is a block diagram of a measuring apparatus for discriminating a paper material of paper according to an embodiment of the invention.

To make the present invention, spectra of near-infrared lights were analyzed with respect to a variety of many paper. Thus, a plurality of wave-lengths showing absorption degree which is peculiar to each paper with respect to the absorption degree have been found out. By obtaining an absorption degree difference by a combination of the absorbances at those wavelengths and using the absorption degree difference, the paper material can be precisely discriminated at a high speed independent of a light/dense pattern caused due to a difference of manufacturing steps, and the paper material of the paper can be discriminated without being influenced by humidity and deterioration in paper material. An embodiment of the invention will now be described hereinbelow with reference to the drawing.

According to the embodiment, the photometric operation is executed by using two kinds of lights belonging to a wavelength range between 800 nm and 2200 nm, aid the paper material of the paper is discriminated by using their photometric values. In the embodiment, such a wavelength range between 800 nm and 2200 nm is referred to as a near-infrared light range.

FIG. 1 shows a measuring apparatus for realizing the invention. This measuring apparatus 1 is built in a bill discriminating apparatus, an automatic bill handling apparatus, or the like (not shown).

The measuring apparatus 1 is constructed by: a light emitting unit 2 for irradiating lights of different wavelengths; a photosensing unit 3 for receiving reflection lights obtaining when the lights emitted from the light emitting unit 2 are reflected by paper; a storing unit 4 for storing a table in which paper materials of the paper and an absorbance difference of the paper materials are stored as a pair; a control unit 5 for calculating the absorbance difference from the reflected lights received by the photosensing unit 3 and discriminating the paper material with reference to the table (not shown) stored in the storing unit 4; and a display unit 6 for displaying a discrimination result of the control unit 5.

The light emitting unit 2 can have two independent light emitting units each for generating a light of a specific wavelength width or can be also constricted so as to generate two wavelengths by a filter. It is also possible to construct the apparatus in a manner such that a plurality of different wavelengths are generated by the light emitting unit 2 and a filler for transmitting the two wavelengths is provided for the photosensing unit.

In the construction of FIG. 1, the absorbance is obtained by the reflecting method of measuring attenuation amounts of the reflected lights which ate obtained when the lights for measurement are reflected by the paper. However, the absorbance can be also obtained by the transmitting method of measuring attenuation amounts of the transmitted lights which are obtained when the lights for measurement pass through the paper. One or those methods can be used. In the embodiment, in both of the transmitting method and the reflecting method the absorbance difference or the absorbance ratio between two wavelengths is used as a parameter for discrimination.

If the two wavelengths which are used are assumed to be D1 and D2 (D1<D2), an absorbance difference DA between two wavelengths is defined by the following equation (1).

$$DA = \mathrm{LOG}(I_{D2}/I_{D2,0}) - \mathrm{LOG}(I_{D1}/I_{D2,0}) \quad (1)$$

where, $I_{D1,0}$, $I_{D2,0}$: light intensity of the reflected light at D1 or D2 when no paper exists $I_{D1}$, $I_{D2}$: light intensity of the reflected light at D1 or D2 when paper exists $I_{D1,0}$, $I_{D2,0}$, $I_{D1}$, $I_{D2}$: light intensity of the transmitted light in case of using the transmitted light Similarly, an absorbance ratio Ar between two wavelengths is defined by the following equation (2).

$$Ar = \mathrm{LOG}(I_{D1}/I_{D1,0}) / \mathrm{LOG}(I_{D2}/I_{D2,0}) \quad (2)$$

As two kinds of lights which are used for the photometric operation, the following points hive been found by analysis or the foregoing spectra. That is, it is most desirable to use wavelengths within ranges of ±30 nm around 1480 nm and 2100 nm as centers respectively, Although wavelength bands of the lights which are used are not particularly limited, it is assumed that the lights within a range between 1 nm and 60 nm can be used.

In the wavelength bands near 1480 nm and 2100 nm, an influence by a variation of absorption of each bill that is caused by the manufacturing step of the lattice-like light/dense pattern as a tint block or the bill is small. Therefore, by using the absorption degree of each paper in those wavelength bands, the paper material itself can be discriminated independent of the lattice-like light/dense pattern. By combining characteristics of the absorption degrees to the lattice-like light/dense pattern at those wavelengths, that is, by using the absorbance difference at those wavelengths, an offset regarding the lattice-like light/dense portions of the bill is performed. Thus, the paper material can be discriminated at further high precision.

Further, in the wavelength bands near 1480 nm and 2100 nm, the absorption intensity difference at each wavelength changes in accordance with a content of amylose (containing amylopectin) in cellulose. Therefore, by obtaining an absorption degree of each bill at each of those wavelengths, the content of amylose can be determined and a material which is used for the bill can be eventually determined.

Absorption due to the absorbed moisture content appears strongly in the range between 1900 nm and 2000 nm. A change in paper material in association with deterioration (increase ill absorption due to yellowing or the like) appears strongly mainly in a visible light range of 800 nm or less. Therefore by measuring the absorption degrees at the above wavelengths, an influence by those environments and an influence by the deterioration are also reduced and more precise discrimination can be made.

A processing flow for paper material discrimination of paper according to the embodiment will now be described with reference to FIG. 2.

First, the light emitting unit 2 irradiates two kinds of lights of different wavelengths to paper as a measurement target (step 11). Subsequently, the photosensing unit 3 receives the reflected lights from the paper (step 12). When the photosensing unit 3 receives the reflected lights, the control unit 5 measures an absorbance spectrum of each of the received reflected lights (step 13) and calculates an absorbance difference between two reflected lights (step 14). The control unit 5 discriminates the paper material of the paper with reference to the correspondence table (not shown) of the paper material and the absorbance difference stored in the storing unit (step 15).

Figure 3:
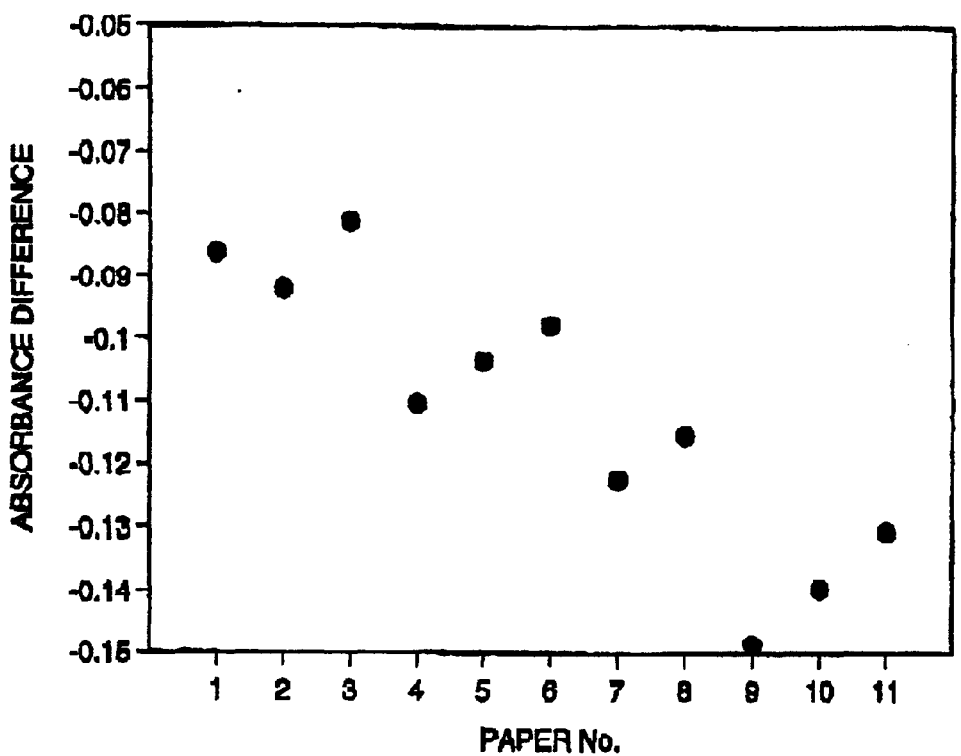
FIG. 3 is a diagram showing an absorbance difference; (reflecting method) of each paper.

FIG. 3 shows measurement results obtained by measuring the absorbance difference between two wavelengths by the reflecting method. As paper, the following pieces of paper are used: that is, normal copy paper (1); color copy paper A (2) and B (3); surface coated paper A (4) and B (5); delumyna paper (6); insulative kraft paper (7); filter paper (8); a bill A (9); a bill B (1C); and a bill C (11). A reference numeral written in ( ) denotes the number of each paper shown on an axis of abscissa in FIG. 3.

Figure 4:
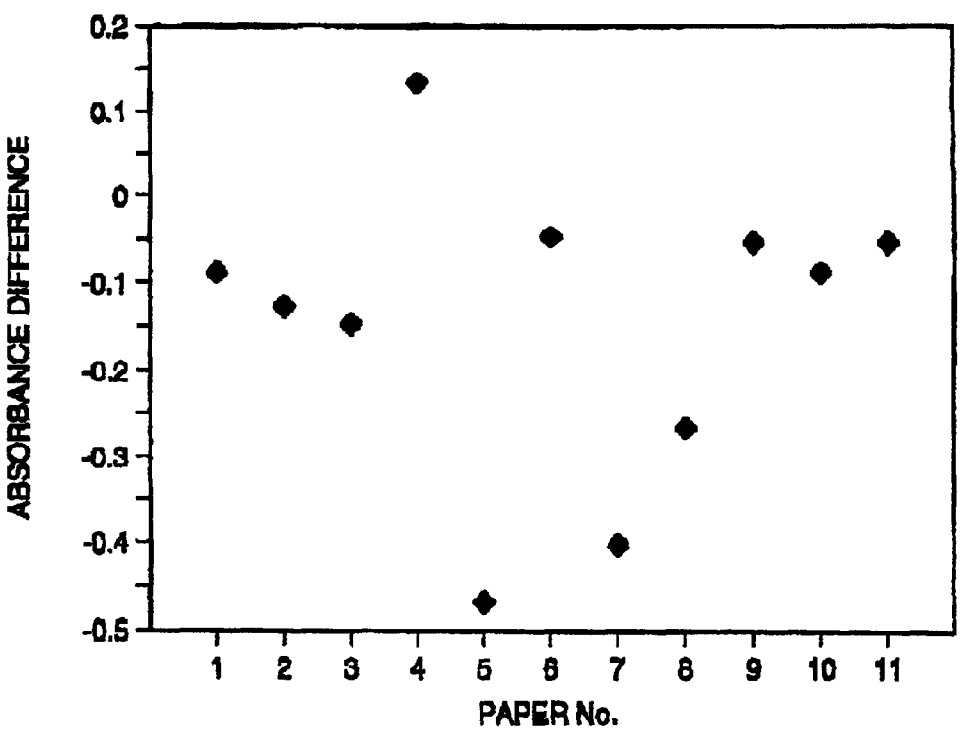
FIG. 4 is a diagram showing an absorbance difference (transmitting method) of each paper.

First, a recording spectrometer in which an integrating sphere unit with a bore of 150 mm has been installed is used as a measuring apparatus. A size of test piece of each discrimination target paper is set to about 50 square mm (however, the bills are used in their own states). (Reflection) absorbance spectra of those test pieces are measured in a wavelength, range between 900 nm and 2200 nm. Absorbances at two wavelengths (1480 nm, 2100 nm) are read out from the obtained spectra and an absorbance difference is calculated by using the above equation (1). Thus, distinct differences could be confirmed in accordance with the paper material of the paper as shown in FIG. 4.

In the experiments, the absorbance spectra have been measured in the wavelength range between 900 nm and 2200 nm the absorbances for two different wavelengths are obtained in the measuring apparatus. As mentioned above, by using the absorbance of each paper for the infrared lights of two specific wavelengths, the high precise discrimination which is hardly influenced by a tint block of the discrimination target paper can be promptly realized by a simple construction. Further, according to the invention, two wavelengths which are effective to determine contents in amylose are used for paper material discrimination. By using such a construction, the paper material is discriminated from the contents in amylose and, further, the bill using such paper can be effectively discriminated.

At a point when the present invention has been made, as a speed of the conveying mechanism of the bill as a discrimination target, a speed in a range between hundreds of sheets per second and thousand and several hundreds sheets per second is required. Therefore, a similar bill discriminating speed is required. In order to make precise discrimination of the paper material at such a high speed, the technique of the embodiment is very effective.

Another embodiment of the invention will now be described. The embodiment which will be described hereinbelow relates to a technique for discriminating a paper material at high precision with respect to paper printed and colored with dye, pigment, or the like having an influence of absorption in a near-infrared range. According to a construction of the embodiment, the printed and colored paper is photometered by using three kinds of lights within a wavelength range between 800 nm and 2200 nm, and in the discrimination of the paper material of the paper, an influence on photometric values by the print or the like performed on the surface of the paper is corrected.

Among the lights which are used for those three kinds of photometric operations, two wavelengths on the long wavelength side become the photometric wavelengths for discriminating the paper material itself of the paper. As such two wavelengths, it is desirable to use wavelengths in ranges within ±30 nm around 1480 nm and 2100 nm as centers, respectively, in a manner similar to the foregoing embodiment. Likewise, wavelength bands of the lights which are used are not particularly limited but a wavelength band between 1 nm and 60 nm can be used, respectively.

The third photometric wavelength as a feature of the embodiment is used for correcting an influence on a photometric value with regard to paper printed and colored with dye, pigment, or the like having an influence of absorption in the near-infrared range. That is, when a reflected light amount is attenuated due to an influence by various dyes and stains, a base of the absorbance spectrum increases. In such a state, since an absorption peak decreases relatively, it is necessary to correct an absolute value by using a reference value.

As a third photometric wavelength mentioned above, in a range between 900 nm and 1000 nm, it is suitable to select a wavelength band in a range between 1 nm and 60 mm. With respect to the wavelength band, it is desirable to use the wavelength band similar to that of the infrared lights for obtaining the reflection degree as mentioned above.

As a photometric method, in a manner similar to the foregoing embodiment, either the reflecting method or the transmitting method can be used without any problem. For both of the transmitting method and the reflecting method, the absorbance difference between the two wavelengths which is expressed by the equation (1) or the absorbance ratio which is expressed by the equation (2) can be used as a parameter for discrimination.

Figure 2:
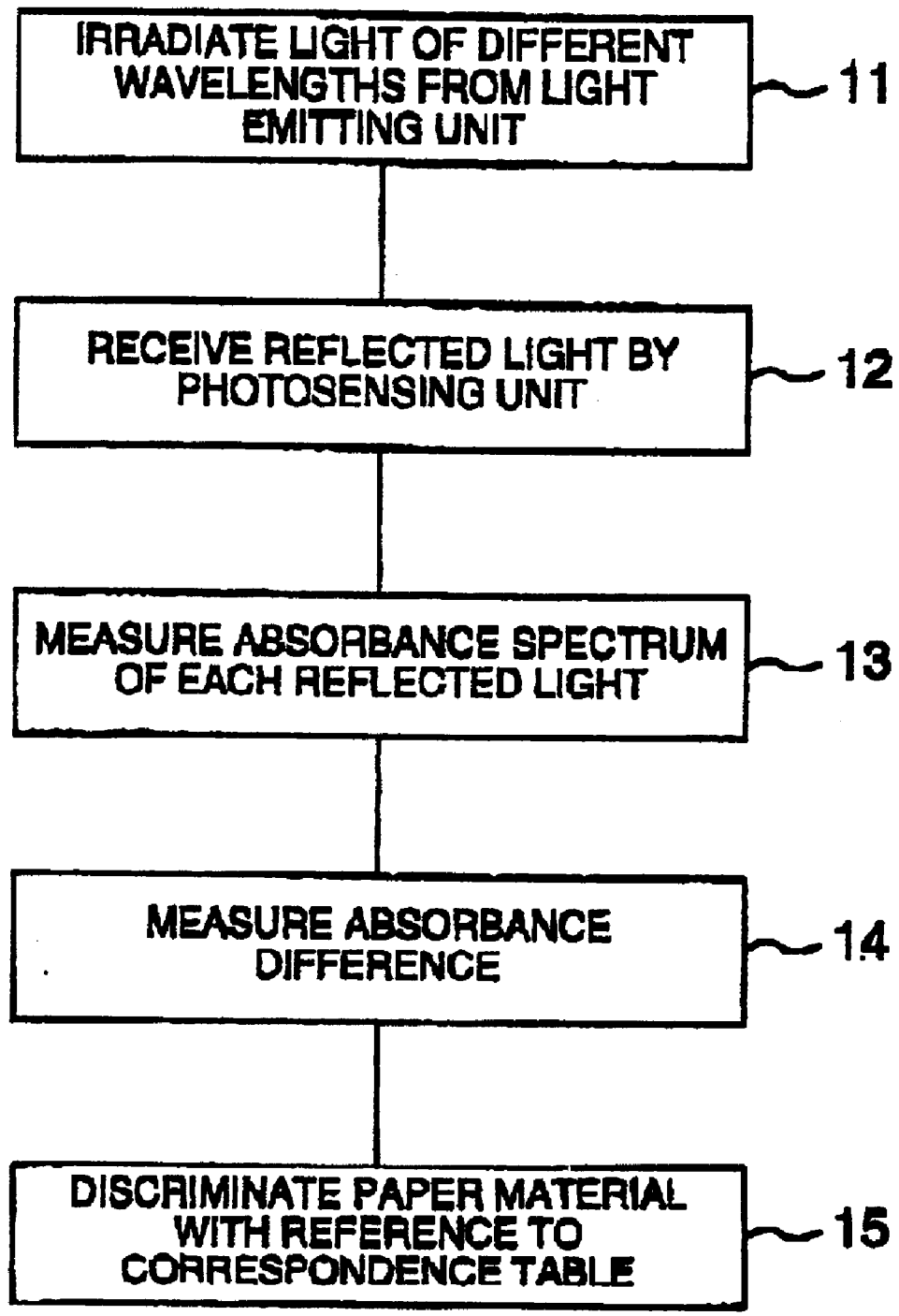
FIG. 2 is flowchart for processes for paper material discrimination of the paper according to the embodiment of the invention.

A measuring apparatus which is used in the embodiment is similar to that shown in FIG. 1 and its processing flow is also similar to that shown in FIG. 2. The embodiment 2 differs from the embodiment 1 with respect to a point such that a portion for executing the correcting process of the photometric value by using the light of the third photometric wavelength with regard to the printed and colored paper is the control unit 5.

The correcting process uses the following equations.

$$\Delta I_R = I_1 - I_2 \quad (3)$$

$$I(\text{New})_1 / I_1 C(\text{Used}) = C \quad (4)$$

$$\text{Correction value } \Delta I_R' = \Delta I_R / C \quad (5)$$

In this case, the absorbance difference between two wavelengths is measured in a manner similar to FIG. 4. Although the absorbance have been derived by using the transmitting method, unlike the case of FIG. 4, a measuring apparatus and a size of each test piece are similar to those upon measurement of FIG. 4. As paper, the following pieces of paper are used: that is, normal copy paper (1); color copy paper A (2) and B (3); surface coated paper A (4) and B (5); delumyna paper (6); insulative kraft paper (7); filter paper (8): a bill A (9); a bill B (10) and a bill C (11).

Figure 5:
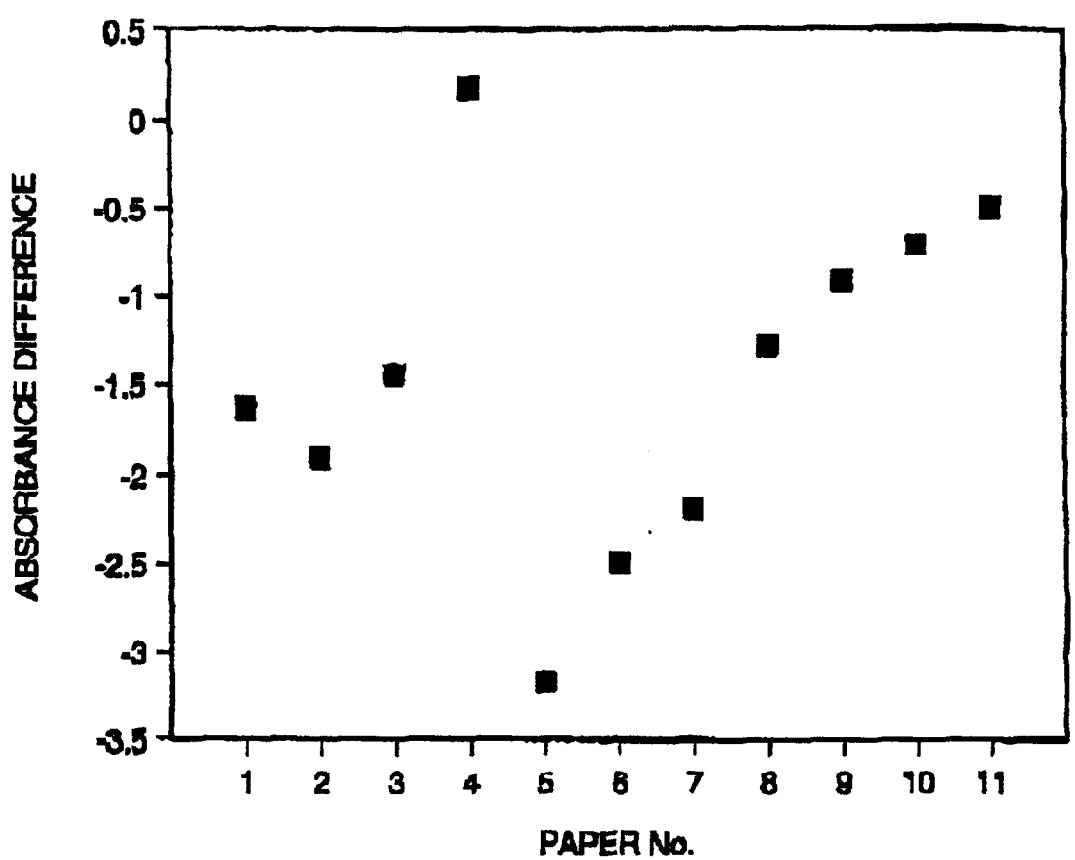
FIG. 5 is a diagram showing an absorbance difference (transmitting method correction).

FIG. 4 shows the absorbance difference (obtained by the transmitting method) of each paper. As shown in FIG. 4, the difference according to the paper material of the paper could be confirmed. However, the test pieces in which the absorbance differences are close although there are absorbance differences exist as shown in the test pieces of Nos. 6, 9, and 11. Therefore, by correcting the above (transmission) absorbance into the absorbance per unit thickness, results as shown in FIG. 5 are obtained. The distinct differences according to the paper material of the paper could be confirmed. As mentioned above, the thickness correction is suitable for paper material discrimination of the paper of different thicknesses.

It should be further understood by those skilled in the art that the foregoing description has been made on embodiments of the invention and that various changes and modifications may be made in the invention without departing from the spirit of the invention and the scope of the appended claims.

What is claimed is:

1. A method for paper material discrimination, comprising the steps of:

irradiating two kinds of lights in near-infrared ranges of different wavelengths onto paper as a measurement target;

obtaining absorbances of the paper to which said two kinds of lights have been irradiated, respectively;

calculating an absorbance difference between said obtained absorbances; and discriminating a paper material of the paper from said calculated absorbance difference on the basis of information in which paper materials of paper and absorbance differences of said paper materials have been made to correspond to each other and which has been stored in memory means, wherein the wavelengths of said two kinds of lights exist within ranges of ±30 nm around 1480 nm and 2100 nm as centers, respectively.

2. A method according to claim 1, wherein reflected lights corresponding to the irradiation of said two kinds of lights are measured and said absorbances are obtained, respectively.

3. A method according to claim 1, wherein transmitted lights corresponding to the irradiation of said two kinds of lights are measured and said absorbances are obtained, respectively.

4. A method according to claim 1, wherein an absorbance ratio is used as said absorbance difference.

5. A method according to claim 1, further comprising the steps of:

irradiating a light of a third kind onto said measurement target paper;

obtaining an absorbance of said third kind of light;

correcting an absorbance of the reflected light of said third kind of light; and discriminating the paper material of the paper from said calculated absorbance difference and said corrected absorbance.

6. A method according to claim 5, wherein a center of a wavelength of said third kind of light exists in a range between 900 nm and 1000 nm.

7. A method according to claim 1, further comprising the steps of detecting a content of amylose in cellulose in said paper material.

8. A method according to claim 1, wherein said discriminating step discriminates said paper material based on a content of amylose in cellulose in said paper material in accordance with a difference between absorption intensities at the wavelengths with respect to said paper material.

9. An apparatus for paper material discrimination, comprising:

a light emitting unit for irradiating two kinds of lights in near-infrared ranges of different wavelengths onto paper as a measurement target;

a photosensing unit for receiving lights necessary for obtaining absorbances of the paper to which said two kinds of lights have been irradiated; and a control unit for calculating an absorbance difference between respective absorbances of said two kinds of lights from the lights received by said photosensing unit and discriminating a paper material of the paper from said calculated absorbance difference on the basis of information in which paper materials of paper and absorbance differences of said paper materials have been made to correspond to each other and which has been stored in memory means, wherein the wavelengths of said two kinds of lights exist within ranges of ±30 nm around 1480 nm and 2100 nm as centers, respectively.

10. An apparatus according to claim 9, wherein said photosensing unit receives reflected lights corresponding to the irradiation of said two kinds of lights, respectively, and said control unit obtains said absorbances from said reflected lights.

11. An apparatus according to claim 9, wherein said photosensing unit receives transmitted lights corresponding to the irradiation of said two kinds of lights, respectively, and said control unit obtains said absorbances from said transmitted lights.

12. An apparatus according to claim 9, wherein said control unit uses an absorbance ratio as said absorbance difference.

13. An apparatus according to claim 9, wherein:

said light emitting unit further irradiates a light of a third kind onto said measurement target paper; and said control unit obtains an absorbance of said third kind of light, corrects said absorbance of said third kind of light, and discriminates a paper material of the paper from said calculated absorbance difference and said corrected absorbance.

14. An apparatus according to claim 13, wherein a center of a wavelength of said third kind of light exists in a range between 900 nm and 1000 nm.

15. An apparatus according to claim 9, wherein said paper is a bill.

16. An apparatus according to claim 9, further comprising means for detecting a content of amylose in cellulose in said paper material.

17. An apparatus according to claim 9, wherein said control unit discriminates said paper material based on a content of amylose in cellulose in said paper material in accordance with a difference between absorption intensities at the wavelengths with respect to said paper material.

18. An apparatus for paper material discrimination, comprising:

a conveying mechanism for conveying a bill;

a measuring mechanism for measuring physical amounts necessary for a first absorbance regarding a first wavelength having a wavelength width around 1480 nm as a center and a second absorbance regarding a second wavelength having a wavelength width around 2100 nm as a center with respect to the bill conveyed by said conveying mechanism;

a storing unit for storing information in which paper materials of bills to be discriminated and a difference between said first and second absorbances have been made to correspond to each other; and a control unit for obtaining the difference between said first and second absorbances from said physical amounts measured by said measuring mechanism and discriminating authenticity of said bill from said information stored in said storing unit.

19. An apparatus according to claim 18, wherein said measuring mechanism measures reflected lights from said bill with respect to said first and second wavelengths.

20. An apparatus according to claim 18, wherein said measuring mechanism measures transmitted lights from said bill with respect to said first and second wavelengths, and said control unit calculates the absorbances regarding said first and second wavelengths from said transmitted lights.

21. An apparatus according to claim 18, wherein a conveying speed of said conveying mechanism is equal to 500 sheets per second.

22. An apparatus according to claim 18, further comprising means for detecting a content of amylose in cellulose in said paper material.

23. An apparatus according to claim 18, wherein said control unit discriminates said paper material based on a content of amylose in cellulose in said paper material in accordance with a difference between absorption intensities at the wavelengths with respect to said paper material.

* * * * *